(12) United States Patent
Reinhart et al.

(10) Patent No.: US 11,830,175 B2
(45) Date of Patent: Nov. 28, 2023

(54) COMPUTER-IMPLEMENTED METHOD FOR MEASURING AN OBJECT

(71) Applicant: Volume Graphics GmbH, Heidelberg (DE)

(72) Inventors: Christof Reinhart, Heidelberg (DE); Daniela Handl, Heidelberg (DE); Sven Gondrom-Linke, Heidelberg (DE); Christoph Poliwoda, Heidelberg (DE); Matthias Flessner, Heidelberg (DE); Thomas Günther, Heidelberg (DE); Sören Schüller, Heidelberg (DE)

(73) Assignee: VOLUME GRAPHICS GMBH, Heidelberg (DE)

( * ) Notice: Subject to any disclaimer, the term of this patent is extended or adjusted under 35 U.S.C. 154(b) by 221 days.

(21) Appl. No.: 17/317,781

(22) Filed: May 11, 2021

(65) Prior Publication Data

US 2021/0350526 A1    Nov. 11, 2021

(30) Foreign Application Priority Data

May 11, 2020 (DE) ...................... 10 2020 112 649.2

(51) Int. Cl.
*G06T 7/00* (2017.01)

(52) U.S. Cl.
CPC .. *G06T 7/0004* (2013.01); *G06T 2207/10116* (2013.01); *G06T 2207/30108* (2013.01)

(58) Field of Classification Search
CPC ......... G06T 7/0004; G06T 2207/10116; G06T 2207/30108; A61B 6/482; A61B 6/032;

(Continued)

(56) References Cited

U.S. PATENT DOCUMENTS

| 6,217,214 B1* | 4/2001 | Cabral | A61B 6/505 |
| | | | 378/208 |
| 2002/0048339 A1* | 4/2002 | Schneider | A61B 6/032 |
| | | | 378/7 |

(Continued)

FOREIGN PATENT DOCUMENTS

| DE | 10 2012 100 150 A1 | 7/2013 |
| DE | 10 2017 208 811 A1 | 11/2018 |

OTHER PUBLICATIONS

Fischer, A et al., "object specific trajectory optimization for industrial x-ray computed tomography" in scientific reports 6(2016) 19135.*

(Continued)

*Primary Examiner* — Sheela C Chawan
(74) *Attorney, Agent, or Firm* — SoCal IP Law Group LLP; Angelo J. Gaz

(57) ABSTRACT

The invention relates to a computer-implemented method for the measurement of an object, wherein the method comprises the following steps: ascertainment of measurement data using a radiographic measurement of the object, wherein the measurement data generates a digital representation of the object with a large number of items of image information of the object; and carrying out the following steps at least before ending the ascertainment of measurement data: analysis of at least one portion of the digital representation of the object; optimization of at least one recording parameter of the radiographic measurement using the analysed portion of the digital representation of the object; and adaptation of the step of ascertainment of measurement data taking the at least one recording parameter into consideration. The invention thus provides a computer-implemented method that has an increased efficiency.

14 Claims, 1 Drawing Sheet

(58) Field of Classification Search
CPC .................. A61B 6/545; G01B 15/045; G01N 2223/423; G01N 23/04; G01N 23/087
USPC ................................................ 382/141, 100
See application file for complete search history.

(56) References Cited

U.S. PATENT DOCUMENTS

| | | | |
|---|---|---|---|
| 2005/0072919 A1* | 4/2005 | Meyer .................. | G01N 23/223 250/307 |
| 2006/0198499 A1 | 9/2006 | Spies et al. | |
| 2016/0232667 A1* | 8/2016 | Taylor .................. | A61M 5/007 |

OTHER PUBLICATIONS

German Patent Office, Examination Report to German Patent Application No. 10 2020 112 649.2, dated Dec. 10, 2020.

\* cited by examiner

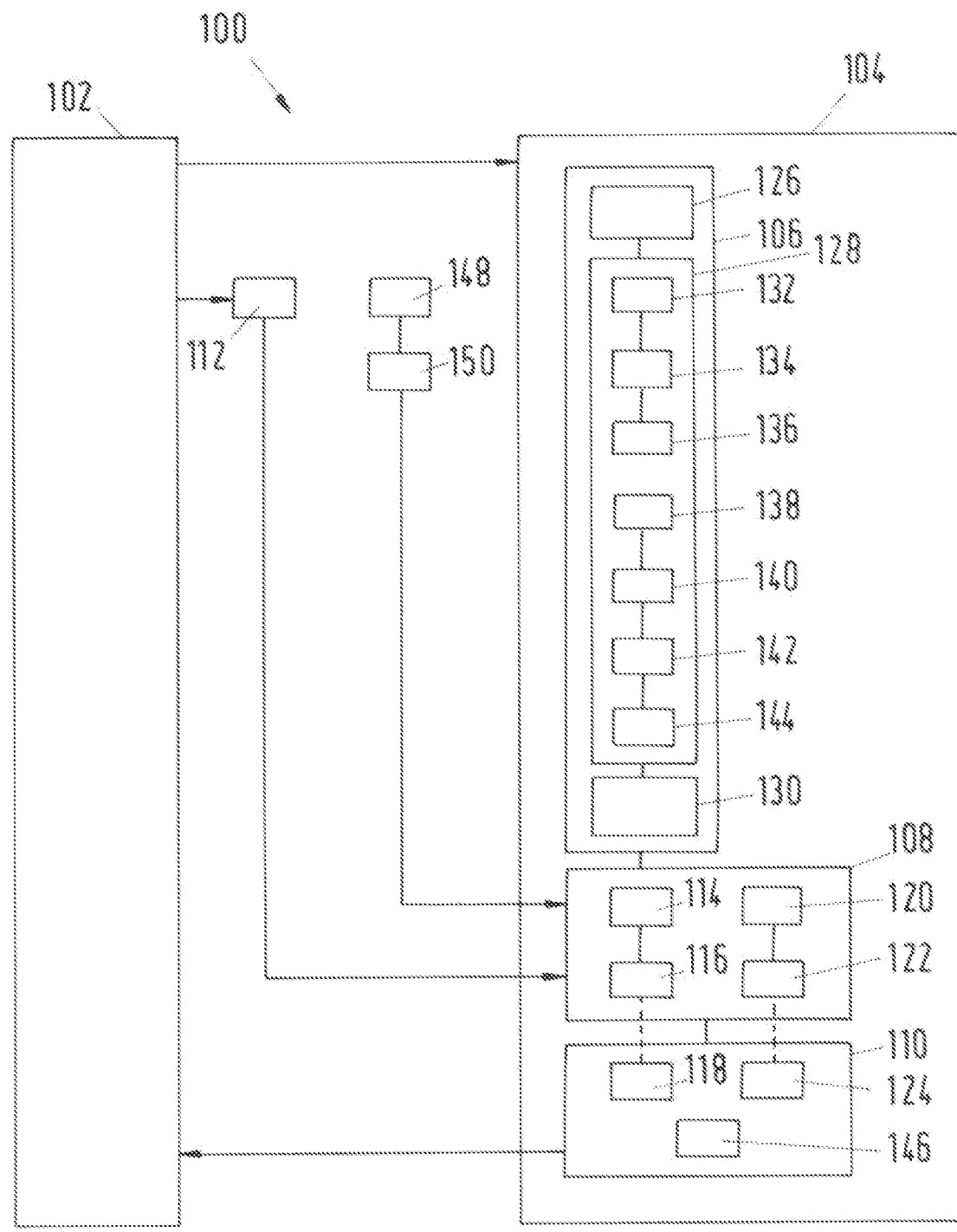

COMPUTER-IMPLEMENTED METHOD FOR MEASURING AN OBJECT

RELATED APPLICATION INFORMATION

This patent claims priority from German Patent Application No. DE 10 2020 112 649.2, filed May 11, 2020 all of which are incorporated herein by reference in their entirety.

BACKGROUND OF THE INVENTION

Field of the Invention

The invention relates to a computer-implemented method for measuring an object.

Description of the Related Art

In the mass production of components, the individual components are subject to manufacturing tolerances in relation to their geometry and possible defects. Measurements are carried out on the components to check whether the tolerances are adhered to and whether defects are present in the component. A component to be measured is initially unknown during the measurement. This can relate to the entire geometry of the component, or only to portions of the geometry of the component. Even when the target geometry is known, the component to be measured has unknown deviations from that, and it is these deviations that often are to be checked.

Defining how the complete ascertainment of the measurement data will be carried out before the start of the measurement is known. Follow-up measurements can, however, be necessary if, during the initial measurement, regions of the component that are required for the ascertainment of the geometry of the component were not acquired with sufficiently high quality.

The object of the invention therefore is to provide a computer-implemented method that has an increased efficiency.

BRIEF SUMMARY OF THE INVENTION

The primary features of the invention are given herein.

In a first aspect the invention relates to a computer-implemented method for measuring an object wherein the method has the following steps: ascertainment of measurement data using a radiographic measurement of the object, wherein the measurement data generates a digital representation of the object with a large number of items of image information of the object; and carrying out the following steps at least before ending the ascertainment of measurement data: analysis of at least one portion of the digital representation of the object; optimization of at least one recording parameter of the radiographic measurement using the analysed portion of the digital representation of the object; and adaptation of the step of ascertainment of measurement data taking the at least one recording parameter into consideration.

In the invention, a computer-implemented method for the measurement of an object is provided that uses information during the ascertainment of the measurement data that emerges from the ascertainment of the measurement data in order to influence the ascertainment of the measurement data. This information can be obtained from an analysis of the object, wherein only a portion of the digital representation must be analysed. The nominal geometry of the object to be measured can be known or unknown before carrying out or starting the measurement. The analysis can here evaluate the object, for example with reference to at least one predefined conformity criterion for the object. The result of the analysis is used to optimize the recording parameter of the radiographic measurement that is used for the ascertainment of the measurement data. The optimization can change the at least one recording parameter here in such a way that the ascertained measurement data is more suitable for the analyses that are to be carried out. It can thus, for example, be determined in the analysis that the surfaces of the analysed portion of the object have only been represented with insufficient accuracy. In this case, the at least one recording parameter can, for example, be optimized in such a way that the representation of the analysed portion of the object is more accurate. The use of the information that emerges from the ascertainment of the measured data can, during ongoing measurement operation of the same object, with the step of adaptation of the step of ascertainment of measurement data, influence the ascertainment of measured data of the object, taking the at least one optimized recording parameter into consideration. The optimization of the recording parameter and the adaptation of the step of ascertainment of measurement data are carried out before ending the step of ascertainment of measurement data. The computer-implemented method thus provides an adaptive measurement of the object that uses the available time efficiently and carries out an optimization of the radiographic measurement during the ascertainment of the measurement data. Inter alia additional measurements are thereby avoided, and the time saved can then, for example, be used to increase the quality of the measurement data of the measurements.

The measurement is a radiographic measurement, for example with x-rays, neutrons or ultrasound. In a radiographic measurement, the analysis can be carried out on the basis of 2D radiographic images, a reconstructed 3D volume, or a combination of both.

Recording parameters of a projection can be the radiographic geometry of the projection and/or setting options that can be set during the radiographic examination of an object, for example current, voltage and pre-filtering of the tubes, the exposure time, the gain factor, the tubes used, e.g. microfocus or nanofocus tubes, the target used, e.g. a reflection or transmission target, the detector used, e.g. area or line detectors, or a possible binning of the detector. If energy-selective detectors are used, the choice of the energy bins can be a setting option.

The digital representation of the object can be a volume representation, a sectional representation, a projection representation and/or a surface representation. The volume representation can, for example, be derived from a plurality of projection representations. The surface representation can, for example, be derived from a volume representation or, in the case of photogrammetry and stripe projection, from a plurality of camera images or measurement images.

The radiographic measurement is carried out using a device that ascertains measurement data from a radiographic geometry around the object. The object is irradiated here from different radiographic directions. A radiographic geometry describes the direction in which radiation is passing through the object, and also the position of the irradiated region and the magnification. Generally speaking the radiographic geometry can be described by the position of the x-ray source and of the detector as seen from the point of view of the measurement object. Nine geometric degrees of freedom results from this: three degrees of freedom each for translation of the tube and the detector, and three degrees of freedom for rotation of the detector. A radiographic geometry can be defined with reference to the measurement object, but also with reference to the device for measuring the object.

The analysis of at least one dimensional measured value of at least one portion of the digital representation of the object can for example be included in the analysis. This can, for example, refer to a reconstruction, a segmentation and/or a surface determination of the measurement data, on the basis of which a further analysis can follow. For example here a dimensional analysis, in particular with reference to dimensions, shape, position, waviness, roughness, wall thicknesses, a target/actual comparison of defined geometries or in defined regions, a defect analysis, in particular for pores, blowholes, inclusions, cracks, porosities or structural loosening, and/or a material analysis, in particular a fibre composite analysis or a foam structure analysis, can be carried out. Alternatively or in addition, an acquisition of the surface, an acquisition of the component interior, i.e. of the material, or an analysis for the completeness of assemblies, for example with respect to a missing element, can further be carried out.

To carry out the analysis in respect of these properties, different approaches can be chosen, for example the evaluation of three-dimensional measurement data that is ascertained from radiographic measurements of an object.

Alternatively or in addition an analysis of two-dimensional measurement data can be carried out. The radiographic measurements can thus also be analysed directly without reconstruction. This can take place directly on unprocessed radiographic images. Multiple radiographic images with different radiographic geometries can also be taken into consideration together here for this purpose.

A reference image can alternatively be used in order to more effectively ascertain possible faults in the images, for example a difference image in relation to a radiographic comparison measurement of a previous measurement on a similar object, which can be averaged, or a difference image with respect to a simulation of an at least similar radiographic examination of the target geometry. In addition to conventional algorithms for defect recognition in two-dimensional measurements, an artificial intelligence can also be trained to identify the faults with greater reliability. It can be advantageous to make use of local information from other sensors for the evaluation, in particular ultrasound, for defect analysis and other material analysis, or optical and tactile sensors for the dimensional metrology.

Once the provisional analysis of the measurement data that is already present has been carried out, this can, for example, be evaluated in particular with reference to the question of whether the necessary quality of the measurement data has already been reached; this does not necessarily have to be carried out globally, but may also be done locally. This can be a global minimum quality of the measurement data specified for the entire measurement volume, or a local minimum quality of the measurement data defined depending on the location or on a property that is to be measured. The minimum quality can here also be ascertained automatically on the basis of the measurement values to be checked, potentially including tolerances, that are specified in an assessment plan. The position of the current measurement result with reference to the tolerance interval is further ascertained. If, in addition, an estimate of the measurement uncertainty is taken into consideration, for example on the basis of the current quality of the measurement data, although also on the basis of empirical values, it is possible to ascertain whether the value is safely inside or outside the tolerance interval. A reliable conclusion as to the necessary quality of the measurement data would thereby already be possible. If this conclusion cannot be reached, further information is necessary in this region. If a minimum quality of the measurement data is not defined, explicitly or implicitly by way of the measurement task, the quality of the measurement data can nevertheless be analysed in order to identify those regions in which the quality of the measurement data is lowest.

It is possible to decide on the basis of this information whether it is still necessary to carry out the measurement again, or whether the information that is present is sufficient to process the defined measurement task. Optimized recording parameters for the subsequent radiographic images can be ascertained here.

A tolerance range that is relevant to the decision regarding the conformity of the component can be specified in each case. The measurements to be carried out are often defined in an assessment plan. A conformity criterion can, for example, be a predefined tolerance that is examined.

The portion of the digital representation of the object is formed from the previously ascertained measurement data.

In many cases a determination of the—possibly local—quality of the measurement data is necessary. In addition, a determination of the local uncertainty resulting from the quality of the measurement data can be performed, and this can be set in relation with the ascertained measurement result and tolerance, as well as the position of the ascertained measurement result within this tolerance. In the case of dimensional metrology, the local volume data can be analysed in order to estimate a local uncertainty of the measurement, for example the position of the surface or of geometric elements adapted to the surface. In the defect analysis and other material analyses, the resolution of the data, for example on the basis of the point spread function, and the noise, for example the signal-to-noise ratio, can, for example, be employed in order to ascertain the quality of the measurement data. From this it is possible to deduce whether details of a certain size, for example small structures, defects or fibres, can be recognized with a particular reliability or uncertainty with the present quality of measurement data. What is known as a "contrast detail detectability" can be derived from this.

In another example of a radiographic measurement, the question posed can be whether, with the quality of the measurement data, the details of the defined size that usually cause variations in the grey level in the measurement data, can be at all distinguished reliably from grey level variations caused by the noise and/or by artefacts.

The quality of the measurement data can further be ascertained using an analysis of the homogeneity of the data in order, for example, to recognize stripes or beam hardening artefacts, and other methods.

Empirical values can furthermore be used for different analyses, in order to estimate the local quality of the measurement data and/or the uncertainty. A certain quality of the measurement data, or uncertainty in the measurement data, can be expected for this purpose in a specific region if this region is acquired from a certain number of radiographic images. This can, for example, be deduced from the specification of the CT system in use.

In a two-dimensional measurement or analysis, an uncertainty can be, for example, derived from recording parameters such as the size of the x-ray spot or the resolution of the detector. Alternatively or in addition, parameters such as the noise or the contrast in the radiographic images can be analysed.

The steps of analysis of at least one portion of the digital representation of the object; optimization of at least one recording parameter of the radiographic measurement using the analysed portion of the digital representation of the object; and adaptation of the step of ascertainment of measurement data taking the at least one recording parameter into consideration can be carried out iteratively.

The step of carrying out the subsequent steps at least before ending the ascertainment of measurement data can be carried out multiple times in sequence with additional or different measurement data obtained through the step of ascertainment of measurement data.

According to one example, during the step of ascertainment of measurement data the method can further comprise the following steps: ascertainment of an estimated material composition and an estimated digital representation of the object using ascertained measurement data of the radiographic measurement of the object; wherein, in the step of optimization of at least one recording parameter of the radiographic measurement, the estimated material composition and the estimated digital representation of the object are taken into consideration.

The ascertainment of the estimated digital representation using the estimated material composition can be carried out for objects comprising mono-materials and multi-materials. The first estimated digital representations do not necessarily have to be used for reconstruction. If an unknown object is to be scanned, no recording parameters are initially known. To determine appropriate parameters, not only are the dimensions of the object of interest, but also the material composition. In the case of metal, for example, higher photon energies are needed than in the case of plastic. An approximate geometry can first be estimated on the basis of initial radiographic images, for example a convex envelope on the basis of the regions at the detector that are not attenuated. Through an analysis of the radiation that is attenuated by the geometry it is possible to estimate what the material composition might be, for example with the support of a list of possible materials. This information can be used to estimate appropriate or optimized recording parameters that, for example, enable an adequate radiographic examination.

In a further example, at least two different spectra can be used for the ascertainment of measurement data in the step of ascertainment of measurement data using a radiographic measurement of the object.

The use of different spectra simplifies this or enables a more accurate ascertainment of the material composition.

According to one further example, the step of optimization of at least one recording parameter of the radiographic measurement using the analysed portion of the digital representation of the object can comprise the following step, wherein the at least one recording parameter comprises at least one setting option and/or at least one radiographic geometry: ascertainment of a radiographic geometry for the radiographic measurement of the object with a maximum transmission length and/or maximum absorption; ascertainment of at least one setting option until a value for a residual radiation that is transmitted through the object along the maximum transmission length lies within a predefined value interval; and wherein the step of adaptation of the step of ascertainment of measurement data taking the at least one recording parameter into consideration comprises the sub-step of: using the at least one ascertained setting option for at least one radiographic geometry in the step of ascertainment of measurement data.

A fundamental rule in the determination of suitable setting options is that a residual radiation should reach the detector everywhere even after transmission through the object. Accordingly, it must still be possible to transmit through even the longest necessary radiographic length according to the radiographic geometry or trajectory. To identify suitable setting options, this radiographic length is, so to speak, tested experimentally. The radiographic geometry is approached here, and the setting options are varied until suitable values are identified. The setting options identified in this way are then so to speak used as a standard or as a starting point for the further ascertainment of the measurement data, or the optimization of the recording parameters. If necessary for other projections, it is again also possible to vary from this standard for the setting options. It can also be helpful to use this setting option for all projections. To identify this radiographic geometry, approximate information about the geometry and, potentially, also about the material composition of the object, is necessary, and this can originate from previous radiographic images. Attention must be paid in the procedure that overexposure of the detector does not occur at the setting option that is to be found. Accordingly, in this radiographic geometry, in the best case non-attenuated radiation should also reach the detector in certain regions, in order to be able to estimate this appropriately. Alternatively, this can be estimated through a further radiographic geometry in which specific regions of the detector are reached by non-attenuated radiation. As a further alternative this can also be estimated through prior knowledge or through simulation. Setting options can, for example, be the current, voltage, pre-filtering of the tubes, the exposure time, the gain factor, the tubes used (e.g. microfocus or nanofocus tubes), the target used (e.g. reflection or transmission target), the detector used (e.g. area or line detector) or a possible binning of the detector.

According to one further example, the step of optimization of at least one recording parameter of the radiographic measurement using the analysed portion of the digital representation of the object can comprise the following step: ascertainment of a provisional digital partial representation of the object from the ascertained measurement data; ascertaining at least one radiographic geometry for the radiographic measurement of the object using the provisional digital partial representation, wherein the radiographic geometry does not have a radiographic length that is longer than a predefined length value, wherein at least radiographic geometries form a subset of the recording parameters, and wherein the step of adaptation of the step of ascertainment of measurement data taking the at least one recording parameter into consideration comprises the sub-step of: using the at least one ascertained radiographic geometry in the step of ascertainment of measurement data.

The radiographic geometries can be identified using a provisional surface or a forward projection on the basis of the reconstruction. The provisional digital partial representation can, for example, be volume data from a provisional reconstruction, or a surface ascertained therefrom. A largest radiographic length can, for example, be ascertained with reference to evaluation of the available measurement data and analysis from the point of view of the geometry, or experimentally in that the region with the greatest attenuation of the x-rays is looked for in various projections from various directions.

The step of analysis of at least one portion of the digital representation of the object can, for example, comprise the following sub-step: ascertainment of at least one portion of a provisional digital representation of the object from the ascertained measurement data; ascertaining at least one region in the at least one portion of the provisional digital representation of the object, wherein the at least one region has a data quality value that is lower than a quality threshold value; ascertaining at least one radiographic geometry for the radiographic measurement of the object, wherein a radiographic measurement is carried out for the at least one region using the at least one radiographic geometry.

In this example the regions which so far have been acquired with an inadequate data quality are analysed with reference to a provisional reconstruction. Those radiographic geometries that cover these regions are identified and preferably used.

Furthermore, for example, the provisional digital partial representation in surrounding regions around surfaces of the object can be analysed in the sub-step of ascertainment of at least one region in the provisional digital partial representation of the object.

In this way, for example, a local quality value can be assigned to the respective surface regions. In the sub-step of ascertainment of at least one region in the at least one portion of the provisional digital representation of the object, the at least one portion of the provisional digital representation can be analysed with regard to a signal-to-noise ratio, a homogeneity and/or a resolution.

In a further example, the sub-step of ascertainment of at least one region in the at least one portion of the provisional digital representation of the object can comprise the following subsidiary sub-steps: ascertaining at least one accuracy value interval for a surface in the digital partial representation; ascertaining an estimated value for the accuracy of the surface; and defining a region around the surface, wherein the region includes the surface, as a region with a data quality value below the quality threshold value if the estimated value lies outside the accuracy value interval.

The provisional reconstruction referred to above can, in particular, be used for the estimation. The use of an analysis of the surrounding regions around the surfaces of the object referred to above is, in principle, also conceivable. The accuracy interval can be defined differently for different material transitions, including when different materials are involved.

According to another example, the sub-step of ascertainment of at least one region in the at least one portion of the provisional digital representation of the object can comprise the following subsidiary sub-steps: ascertaining a user-defined minimum quality threshold value for a region in the at least one portion of the provisional digital representation, wherein the at least one portion of the provisional digital representation comprises volume data; ascertaining a data quality value for the region; comparing the data quality value with the user-defined minimum quality threshold value; and defining the region as a region with a data quality value below the quality threshold value if the data quality value is lower than the quality threshold value.

For this purpose, the analysis of the surrounding regions around the surfaces of the object described above can in particular be used for the analysis. The quality threshold value can be defined differently for different materials. The quality threshold value can also be defined by measures relevant to the application, such as "defects with a size of 20 µm must be detectable"; alternatively, the quality threshold value can also be defined with the aid of "contrast detail detectability".

The step of adaptation of the step of ascertainment of measurement data can further, for example, comprise the following sub-step: ending the step of ascertainment of measurement data if the digital representation of the object does not have a data quality value that is lower than the quality threshold value.

This is, for example, the case if all the ascertained measurement data have a data quality that satisfies a minimum data quality. The ascertainment of the measurement data is then ended automatically.

In the step of adaptation of the step of ascertainment of measurement data, the at least one region can be defined as a region with a data quality value that is greater than the quality threshold value if an ascertained conformity result relating to the analysed portion of the digital representation of the object shows that the at least one portion of the digital representation of the object, taking the measurement data, the data quality and at least one predefined conformity criterion into consideration, fully satisfies the at least one predefined conformity criterion.

This means that as soon as the whole object has been acquired with the desired minimum quality, or the data quality described above is adequate everywhere, the ascertainment of the measurement data is ended automatically. It is possible here to assess whether, taking the data quality or an uncertainty of the measurement derived therefrom into consideration, the current measurement result fully or reliably satisfies the predefined conformity criterion that can, for example, define a tolerance range.

In a further example, the method can comprise the step of carrying out the following steps: analysis of at least one portion of the digital representation of the object; optimization of at least one recording parameter of the radiographic measurement using the analysed portion of the digital representation of the object; and adaptation of the step of ascertainment of measurement data taking the at least one recording parameter into consideration; carried out while the step of ascertainment of measurement data is carried out.

Further radiographic images are recorded simultaneously while the ascertainment of the optimized recording parameters is carried out. It takes a relatively long time to carry out the evaluations and to identify optimized recording parameters or to make a decision as to whether further radiographic images are at all necessary. No updated or optimized recording parameters are thus present in the meantime. Instead of waiting until these calculations are concluded in order only then to record further radiographic images, further radiographic images can be recorded during the evaluation. In the time required for the calculations, for example ten to twenty additional images can be recorded. Since, however, no optimized recording parameters are yet present, recording parameters can, for example, be chosen that originate from the previous iteration, and which have a lower optimization than the recording parameters that are present after concluding the calculation.

In a further example, the method can comprise the following further step: ascertainment of a predefined maximum measurement duration for the step of ascertainment of measurement data; carrying out the step of optimization of at least one recording parameter of the radiographic measurement using the analysed portion of the digital representation of the object in such a way that the step of analysis of at least one portion of the digital representation of the object using the optimized recording parameter supplies more accurate analysis results within the duration of the measurement than when other recording parameters are used.

A user can thus define a maximum time duration for the ascertainment of the measurement data of the object. In the optimization of the recording parameters, the solution that supplies the most accurate or best results within the framework of this time duration is sought.

In a further aspect, the invention relates to a computer program product with instructions that are executable on a computer which, when executed on a computer, cause the computer to carry out the method according to the preceding description.

Advantages and effects as well as further developments of the computer program product emerge from the advantages and effects as well as the further developments of the method described above. Reference is therefore made in this respect to the description above. A computer program product can, for example, refer to a data carrier on which a computer program element is stored that contains instructions that are executable for a computer. Alternatively or in addition a computer program product can, for example, also refer to a permanent or volatile data memory such as a flash memory or a working memory that contains the computer program element. Other types of data memory that contain the computer program element are not, however, thereby excluded.

Further features, details and advantages of the invention emerge from the wording herein as well as from the following description of exemplary examples with reference to the drawings, in which

BRIEF DESCRIPTION OF THE SEVERAL VIEWS OF THE DRAWING(S)

FIG. 1 shows a flow diagram of the computer-implemented method.

DETAILED DESCRIPTION OF THE INVENTION

The computer-implemented method for the measurement of an object is referenced below in its entirety, as denoted in FIG. 1, with the reference sign 100.

In a first step 102, the method 100 comprises the ascertainment of measurement data using a device for the measurement of the object. The measurement data here generate a digital representation of the object that comprises a plurality of image information items of the object. This can, for example, be a two-dimensional representation of the object or a three-dimensional representation of the object. The digital representation of the object can equally be derived from measurement data, for example, in the case of radiographic measurements, through a tomographic reconstruction.

A further step 104 is carried out at least before ending step 102. Step 104 can here interrupt step 102. Alternatively, step 104 can be carried out before ending step 102 simultaneously with step 102, i.e. be carried out during step 102. At this point in time, not all of the measurement data that are to be ascertained have yet been ascertained about the object. This means that only a portion of the digital representation of the object is present. Step 104 here comprises steps 106, 108 and 110.

In step 106, the at least one portion of the digital representation of the object is analysed. This is the portion of the digital representation of the object that has been ascertained up to now by step 102, since step 102 has not yet ended when step 106 is carried out. Measurement data used in step 106 are at first provisional measurement data, since step 102 continues to be carried out. Here, in step 106, for example, a dimensional measurement value can be analysed for predefined conformity criteria. The provisional measurement data, which can be surface data and/or volume data, are analysed.

Step 106 can comprise the optional sub-steps 126, 128 and 130.

In the optional sub-step 126, a provisional digital representation of the object is ascertained from the measurement data ascertained in step 102. At least a portion of the digital representation is ascertained here. The ascertainment can, for example, comprise alignment of the measurement data and/or a surface ascertainment. The provisional digital representation of the object is inaccurate compared to a digital representation generated after step 102 has ended with a complete set of ascertained measurement data. For a provisional analysis that is carried out in step 106, the provisional digital representation of the object is, however, sufficient.

In the optional sub-step 128 at least one region is ascertained in the at least one portion of the provisional digital representation of the object. The ascertainment of the region here evaluates the positions in the object at which the ascertained measurement data have data quality values that are less than a characteristic quality value. The characteristic quality value here indicates a minimum quality. If the quality values are measured with an inverse scale, i.e. if low values are better than high values, then the ascertainment of the region evaluates the position at which the measurement data have data quality values that are higher than the characteristic quality value.

For the ascertainment of the data quality values, surrounding regions around the surfaces of the object can, for example, be analysed in the provisional digital partial representation. In this way, firstly, a larger quantity of measurement data is available for the analysis. Secondly, structures that are for example disposed underneath the surface of an object also give indications of the data quality of the ascertained measurement data.

Further, to ascertain the data quality, the signal-to-noise ratio of the measurement data ascertained so far that underlie the provisional partial representation of the object can, for example, be evaluated. Alternatively or in addition, the homogeneity of the measurement data and/or their resolution can be evaluated.

In the optional sub-step 130, at least one radiographic geometry is ascertained for the radiographic measurement of the object. For the at least one region of the at least one portion of the provisional digital representation of the object, in which the measurement data have a data quality that lies below the quality threshold value, a radiographic measurement is carried out using the at least one radiographic geometry. In this way additional measurement data that either have a better data quality and/or that improve the data quality in combination with the measurement data ascertained so far can be ascertained for regions in which the data quality of the measurement data ascertained so far is not sufficient to carry out accurate analyses.

The optional sub-step 128 can comprise the optional subsidiary sub-steps 132, 134 and 136.

The subsidiary sub-step 132 here relates to the ascertainment of an accuracy value interval for a surface in the digital partial representation. The accuracy value interval can here, for example, be predefined and, for example, depend on the material composition of the object. Thus, for example, a particular accuracy value interval can be defined for a particular surface that bounds a specific material with respect to the surroundings of the object, i.e. the external air. A different accuracy value interval can be defined for a surface that is disposed inside the object and that separates two materials from one another. A specific accuracy value interval is ascertained depending on the surface.

In the subsidiary sub-step 134, the accuracy of the surface is estimated, and an estimated value is ascertained for the accuracy. An estimated value can, for example, be ascertained here for each point on the surface, and a mean value or a median can be generated for the overall surface. Other ascertainment methods for the estimated value are also conceivable.

Following this, in subsidiary sub-step 136, an analysis is performed as to whether the ascertained estimated value lies within or outside the accuracy value interval. If the estimated value lies outside the accuracy value interval, a region around the surface being evaluated is defined. A data quality value that lies below the quality threshold value is further assigned to this region. This means that when the estimation indicates that the surface is inaccurate, the data quality in the region around this surface is also evaluated as insufficient.

The sub-step 128 can further comprise the subsidiary sub-steps 138, 140, 142 and 144.

In subsidiary sub-step 138 a user-defined minimum quality threshold value that applies to a region of the provisional digital representation is ascertained. The provisional digital representation here comprises volume data that can, for example, be generated from the measurement data of a radiographic measurement using a tomographic calculation.

The user-defined minimum quality threshold value can here, for example, be obtained through a user input. Alternatively or in addition, a user can specify in advance minimum quality threshold values for different regions.

A data quality value is ascertained in subsidiary sub-step 140 for the region for which the user-defined minimum quality threshold value has been ascertained. The ascertainment of the data quality value can, for example, be performed here using the subsidiary sub-steps 132, 134 and 136. Alternatively or in addition, the data quality can be evaluated, as explained above, for example using the signal-to-noise ratio, the homogeneity of the measurement data and/or their resolution. Further methods for the ascertainment of the data quality are also conceivable.

The data quality value that has been ascertained for the region is compared to the minimum quality threshold value of the region in subsidiary sub-step 142. Whether the data quality value lies above or below the quality threshold value is thereby ascertained. If the data quality value lies above the quality threshold value, the measurement data in the region reach a minimum quality.

If the data quality value lies below the quality threshold value, the measurement data in the region do not reach the minimum quality. In this case, this region is defined as a region with a data quality value below the quality threshold value in subsidiary sub-step 144.

Step 108 is carried out after step 106. At least one recording parameter of the radiographic measurement is optimized in step 108. The optimization here takes place using the analysed portion of the digital representation of the object. This means that the evaluations carried out in step 106 enter into the optimization of the recording parameter. A recording parameter can thus, for example, be changed in such a way that the regions in which the ascertainment of the measurement data achieved so far only results in a data quality that lies below a quality threshold value are measured using other radiographic geometries that achieve an improved data quality. Measurement data that represents the regions of the object with small structures tend to be measured with a greater magnification and/or a larger number of radiographic images of the radiographic measurement in order to be able to analyse these small structures appropriately. In a similar way, a target geometry of the object can be analysed in respect of small structures that are to be measured, in order to identify these regions.

In the optimization of the recording parameters, consideration is given to whether certain radiographic geometries have a greater uncertainty in the geometric calibration as a result of the kinematics of the CT system.

The optimized recording parameters are used in step 110 to adjust step 102 appropriately.

Step 108 can here comprise sub-steps 114 and 116. In this connection, step 110 can comprise sub-step 118. A recording parameter here comprises at least one radiographic geometry and/or at least one setting option for the radiographic measurement.

In sub-step 114, a radiographic geometry for the radiographic measurement of the object in which a maximum radiographic length is achieved is ascertained. Alternatively or in addition, the radiographic geometry in which a maximum absorption by the object is brought about can be ascertained.

A setting option is ascertained in sub-step 116 for this radiographic geometry, in which a residual radiation of the radiation used for the radiographic measurement lies within a predefined value interval after the transmission through the object. In this way, with the ascertained setting option, a minimum radiation intensity for the radiation source that must at least be present for the whole of the radiographic measurement so that a residual radiation is always obtained after radiographic transmission through the object can be ascertained. A complete absorption of the radiation during the radiographic transmission through other regions of the object is thus avoided.

The measurement data that has already been ascertained, for example radiographic images that have already been recorded, can further be analysed. If a sufficient radiographic transmissibility is not possible in some of these cases, the corresponding radiographic images can be removed from the reconstruction. These radiographic images could cause artefacts. In addition, alternative radiographic images with similar radiographic geometry can instead be recorded, for example if in the surroundings a geometry with lower transmission is available, and/or with varying setting options, in particular current, voltage or exposure time.

If the radiographic measurement is carried out using a robot CT system, and as soon as a plurality of new radiographic geometries and/or setting options is specified, a search is made for a trajectory with which the ascertainment of the measurement data requires as little time as possible. Care is taken to ensure here that the robot CT system travels the shortest possible distances, or that the voltage is varied as rarely as possible.

In sub-step 118, which is carried out in step 110, the at least one setting option that has been ascertained in sub-step 116 is used to ascertain measurement data in step 102. The setting option for at least one of the radiographic geometries that are subsequently used by step 102 for the ascertainment of measurement data is set here.

Alternatively or in addition, step 108 can comprise the sub-steps 120 and 122. In this connection, step 110 can include sub-step 124.

In sub-step 120, a provisional digital partial representation of the object is ascertained from the measurement data ascertained in step 102. This can, for example, be a reconstruction of volume image data from projection image data. Since step 102 has not yet ended, not all the measurement data of the object have yet been ascertained. The ascertained digital partial representation of the object is therefore initially provisional.

The provisional digital partial representation of the object is used in sub-step 122 to ascertain at least one radiographic geometry for the radiographic measurement of the object. The at least one radiographic geometry ascertained in this sub-step here is a subset of the recording parameters used. In the ascertainment of the at least one radiographic geometry, a radiographic geometry that only has radiographic lengths that are less than a predefined length value is selected. The radiographic geometry thus does not have any radiographic lengths that are longer than the predefined length value.

These ascertained radiographic geometries are used in sub-step 124, which is carried out in step 110, to adapt step 102. The ascertained radiographic geometries are here used in step 102 for the ascertainment of measurement data.

In this way, radiographic lengths with which no residual radiation, or only an insufficient fraction thereof, would remain after the radiographic transmission through the object as a result of the total radiation or a high proportion of the radiation being absorbed in the object, are avoided in the ascertainment of the measurement data in step 102. This improves the data quality of the measurement data, since in any event a sufficiently high residual radiation remains after the radiographic transmission through the object.

Step 110 can, further, comprise the sub-step 146 in which step 102 is ended if the digital representation of the object, or the digital partial representation of the object, has a data quality value that is sufficient. Data quality values for all the measurement data are ascertained for this purpose, and tested against a quality threshold value. If none of the data quality values of the measurement data lie below the quality threshold value, then sufficiently good measurement data are present to allow an accurate analysis to be carried out. A further ascertainment of measurement data would not increase the accuracy of the analysis any further. In this case the ascertainment of the measurement data can be ended in order to save time and potentially to be able to measure a further object.

The method 100 can further comprise the optional step 112 that is carried out during step 102 and can adapt step 108.

In step 112, estimates are made as to what material the measured object comprises. The material composition is estimated using the measurement data that was ascertained in step 102. An estimated digital representation of the object is further ascertained using the ascertained measurement data. In this way carrying out an estimate of the measured object with the available measurement data is thus already started before the ascertainment of the measurement data in step 102 is ended.

In step 108, the estimated material composition and the estimated digital representation of the object are taken into account in order to optimize the recording parameters for the radiographic measurement.

If a radiographic measurement is to be carried out with the minimum activity on the part of a user, it is possible to further estimate, for example with reference to the existing measurement data, which reconstruction algorithm supplies the best results. With a small number of radiographic images it is for example possible to choose an iterative method, while with circular trajectories with a large number of radiographic images, the filtered back-projection can be the better choice.

It is further possible to estimate on the basis of the available measurement data whether a correction method, for example to correct for radiation hardening, stray radiation and/or an incorrect geometrical alignment of the apparatus for carrying out the method, should be carried out. This can then be done automatically. It is further, for example, possible to identify whether an interaction with a user is necessary, for example in order to reposition the object on the turntable, to use a contrast agent, or to remove a highly absorbent part such as a radiation screw.

The method 100 can further comprise the optional steps 148 and 150.

In optional step 148, a maximum measurement duration for step 102 is ascertained. The maximum measurement duration here is predefined, and states the period of time within which step 102 is carried out, i.e. in which an ascertainment of measurement data of the object should take place.

The predefined measurement duration that is ascertained in step 148 is used in step 150. Step 150 here alters step 108 in such a way that the recording parameters optimized in step 108 are optimized taking the predefined measurement duration into consideration. The measurement data ascertained subsequently with the optimized recording parameters have the effect that step 106 already delivers more accurate analysis results than when other recording parameters are used during the measurement duration, i.e. while step 102 is still being carried out.

The computer-implemented method 100 can be carried out using a computer program product on a computer. The computer program product here comprises instructions that can be executed on a computer. If these instructions are executed on a computer, they cause the computer to carry out the method.

The invention is not restricted to one of the above-described forms of embodiment, but can be modified in a variety of ways. All of the features and advantages emerging from the claims, the description and the drawing, including constructive details, spatial arrangements and method steps, can be significant to the invention, both in themselves as well as in a wide variety of combinations.

The invention claimed is:

1. A computer-implemented method for the measurement of an object, wherein the method comprises the following steps:
   ascertainment of measurement data using a radiographic measurement of the object, wherein the measurement data generates a digital representation of the object with a large number of items of image information of the object; and
   carrying out the following steps at least before ending the ascertainment of measurement data:
     analysis of at least one portion of the digital representation of the object;
     optimization of at least one recording parameter of the radiographic measurement using the at least one analysed portion of the digital representation of the object, characterized in that the step of optimization of at least one recording parameter of the radiographic measurement using the at least one analysed portion of the digital representation of the object comprises the following step, wherein the at least one recording parameter comprises at least one setting option and/or at least one radiographic geometry:
       ascertainment of the at least one radiographic geometry for the radiographic measurement of the object with a maximum radiographic length and/or maximum absorption;

ascertainment of at least one setting option until a value for a residual radiation that is transmitted through the object along the maximum radiographic length lies within a predefined value interval; and adaptation of the step of ascertainment of measurement data taking the at least one recording parameter into consideration, wherein the step of adaptation of the step of ascertainment of measurement data taking the at least one recording parameter into consideration comprises the sub-step of:

using the at least one ascertained setting option for the at least one radiographic geometry in the step of ascertainment of measurement data.

2. Method according to claim 1, characterized in that the method, during the step of ascertainment of measurement data further comprises the following steps:

ascertainment of an estimated material composition and an estimated digital representation of the object using ascertained measurement data of the radiographic measurement of the object;

wherein, in the step of optimization of at least one recording parameter of the radiographic measurement, the estimated material composition and the estimated digital representation of the object are taken into consideration.

3. Method according to claim 1, characterized in that at least two different spectra are used for the ascertainment of measurement data in the step of ascertainment of measurement data using a radiographic measurement of the object.

4. Method according to claim 1, characterized in that the step of carrying out the steps of: analysis of at least one portion of the digital representation of the object; optimization of at least one recording parameter of the radiographic measurement using the at least one analysed portion of the digital representation of the object; and adaptation of the step of ascertainment of measurement data taking the at least one recording parameter into consideration are carried out while the step of ascertainment of measurement data is carried out.

5. Method according to claim 1, characterized in that the method comprises the following further steps:

ascertainment of a predefined maximum measurement duration for the step of ascertainment of measurement data;

carrying out the step of optimization of at least one recording parameter of the radiographic measurement using the at least one analysed portion of the digital representation of the object in such a way that the step of analysis of at least one portion of the digital representation of the object using the optimized recording parameter supplies more accurate analysis results within the duration of the measurement than when other recording parameters are used.

6. A non-transitory computer readable storage medium with instructions that can be executed on a computer which, when executed on a computer cause the computer to carry out the method according to claim 1.

7. A computer-implemented method for the measurement of an object, wherein the method comprises the following steps:

ascertainment of measurement data using a radiographic measurement of the object, wherein the measurement data generates a digital representation of the object with a large number of items of image information of the object; and carrying out the following steps at least before ending the ascertainment of measurement data:

analysis of at least one portion of the digital representation of the object;

optimization of at least one recording parameter of the radiographic measurement using the at least one analysed portion of the digital representation of the object, characterized in that the step of optimization of at least one recording parameter of the radiographic measurement using the at least one analysed portion of the digital representation of the object comprises the following sub-steps;

ascertainment of a provisional digital partial representation of the object from the measurement data ascertained:

ascertainment of at least one radiographic geometry for the radiographic measurement of the object using the provisional digital partial representation, wherein the at least one radiographic geometry does not have a radiographic length that is longer than a predefined length value, wherein the at least radiographic geometry forms a subset of the recording parameters; and adaptation of the step of ascertainment of measurement data taking the at least one recording parameter into consideration, wherein the step of adaptation of the step of ascertainment of measurement data taking the at least one recording parameter into consideration comprises the sub-step of:

using the at least one ascertained radiographic geometry in the step of ascertainment of measurement data.

8. Method according to claim 7, characterized in that the step of adaptation of the step of ascertainment of measurement data comprises the following sub-step:

ending the step of ascertainment of measurement data if the digital representation of the object does not have a data quality value that is lower than the quality threshold value.

9. Method according to claim 7, characterized in that in the step of adaptation of the step of ascertainment of measurement data, the at least one region is defined as a region with a data quality value that is greater than the quality threshold value if an ascertained conformity result relating to the at least one analysed portion of the digital representation of the object shows that the at least one portion of the digital representation of the object, taking the measurement data, the data quality and at least one predefined conformity criterion into consideration, fully satisfies the at least one predefined conformity criterion.

10. A computer-implemented method for the measurement of an object, wherein the method comprises the following steps:

ascertainment of measurement data using a radiographic measurement of the object, wherein the measurement data generates a digital representation of the object with a large number of items of image information of the object; and carrying out the following steps at least before ending the ascertainment of measurement data:

analysis of at least one portion of the digital representation of the object, characterized in that the step of analysis of at least one portion of the digital representation of the object comprises the following sub-steps:

ascertainment of at least one portion of a provisional digital representation of the object from the measurement data ascertained;

ascertainment of at least one region in the at least one portion of the provisional digital representation of the object, wherein the at least one region has a data quality value that is lower than a quality threshold value;

ascertainment of at least one radiographic geometry for the radiographic measurement of the object, wherein a radiographic measurement for the at least one region is carried out using the at least one radiographic geometry;

optimization of at least one recording parameter of the radiographic measurement using the at least one analysed portion of the digital representation of the object; and adaptation of the step of ascertainment of measurement data taking the at least one recording parameter into consideration.

11. Method according to claim 10, characterized in that the provisional digital partial representation in surrounding regions around surfaces of the object is analysed in the sub-step of ascertainment of at least one region in the provisional digital partial representation of the object.

12. Method according to claim 10 characterized in that in the sub-step of ascertainment of at least one region in the at least one portion of the provisional digital representation of the object, the at least one portion of the provisional digital representation is analysed with regard to a signal-to-noise ratio, a homogeneity and/or a resolution.

13. Method according to claim 10, characterized in that the sub-step of ascertainment of at least one region in the at least one portion of the provisional digital representation of the object comprises the following subsidiary sub-steps:

ascertainment of at least one accuracy value interval for a surface in the digital partial representation;

ascertainment of an estimated value for the accuracy of the surface; and definition of a region around the surface, wherein the region comprises the surface, as a region with a data quality value below the quality threshold value if the estimated value lies outside the accuracy value interval.

14. Method according to claim 10, characterized in that the sub-step of ascertainment of at least one region in the at least one portion of the provisional digital representation of the object comprises the following subsidiary sub-steps:

ascertainment of a user-defined minimum quality threshold value for a region in the at least one portion of the provisional digital representation, wherein the at least one portion of the preliminary digital representation comprises volume data;

ascertainment of a data quality value for the region;

comparison of the data quality value with the user-defined minimum quality threshold value; and definition of the region as a region with a data quality value below the data quality threshold value if the data quality value is less than the quality threshold value.

* * * * *